United States Patent [19]

Termanini

[11] Patent Number: 5,474,634

[45] Date of Patent: Dec. 12, 1995

[54] PROTECTIVE TAPE

[76] Inventor: Zafer Termanini, 208 Eileen Dr., Cedar Grove, N.J. 07009

[21] Appl. No.: 243,640

[22] Filed: May 17, 1994

[51] Int. Cl.$^6$ .......................... B32B 31/18; A61B 17/15
[52] U.S. Cl. ............... 156/250; 428/40; 428/354; 602/9; 602/52; 602/57
[58] Field of Search ................ 428/40, 343, 354, 428/355; 427/208; 602/52, 57, 58, 9; 156/250

[56] References Cited

U.S. PATENT DOCUMENTS

| | | | |
|---|---|---|---|
| Re. 24,906 | 12/1960 | Ulrich | 427/208 X |
| Re. 31,887 | 5/1985 | Hodgson | 602/52 X |
| 2,411,237 | 6/1943 | Turner et al. | 427/208 X |
| 2,599,359 | 6/1952 | Banks et al. | 427/208 X |
| 4,839,206 | 6/1989 | Waldenberger | 427/208 X |
| 5,130,185 | 7/1992 | Ness | 427/208 X |

*Primary Examiner*—Jenna L. Davis
*Attorney, Agent, or Firm*—Ralph T. Lilore

[57] ABSTRACT

Disclosed is a device in the form of an adhesive tape stripping which in consequence of its configuration and presence of glue surfaces thereon facilitates the isolation of sawed particles of a cast material, for example, to the area of cutting as the material is being cut or sawed. Thus, for example, when a casting material is ready to be removed from a limb, the protective tape of the invention is applied to the cast in such a manner as to orient the cutting path preferably along the center of the tape. In a preferred case, a guide line is drawn on the tape for such purpose. The process of cutting generates the particles which instead of being dispersed into the atmosphere are accumulated on the adhesive surfaces of the trapping tape and are also embedded into the body of a thicker bottom adhesive layer of the tape thereby obviating the need for any vacuum equipment material and the associated personnel required therefor.

6 Claims, 2 Drawing Sheets

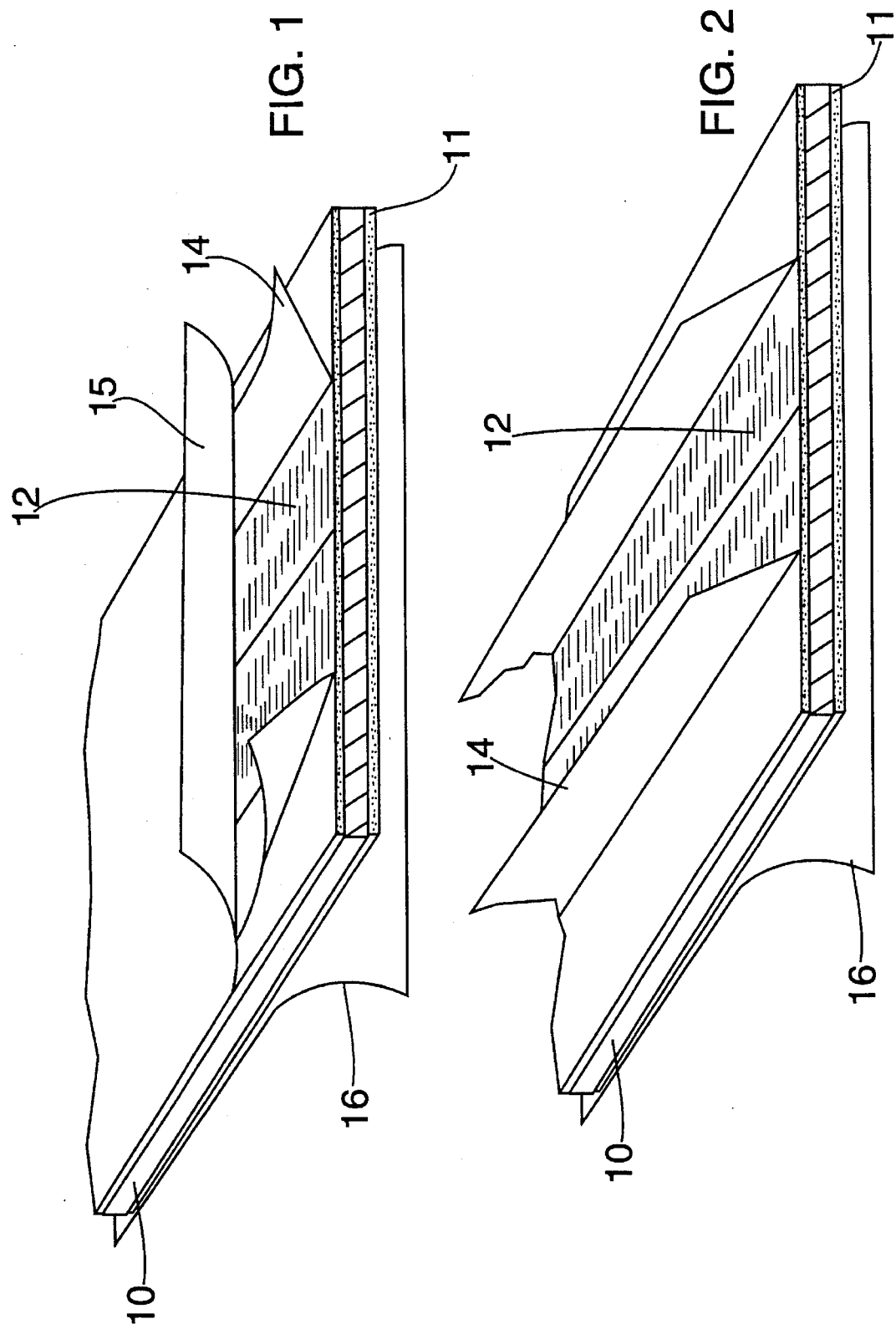

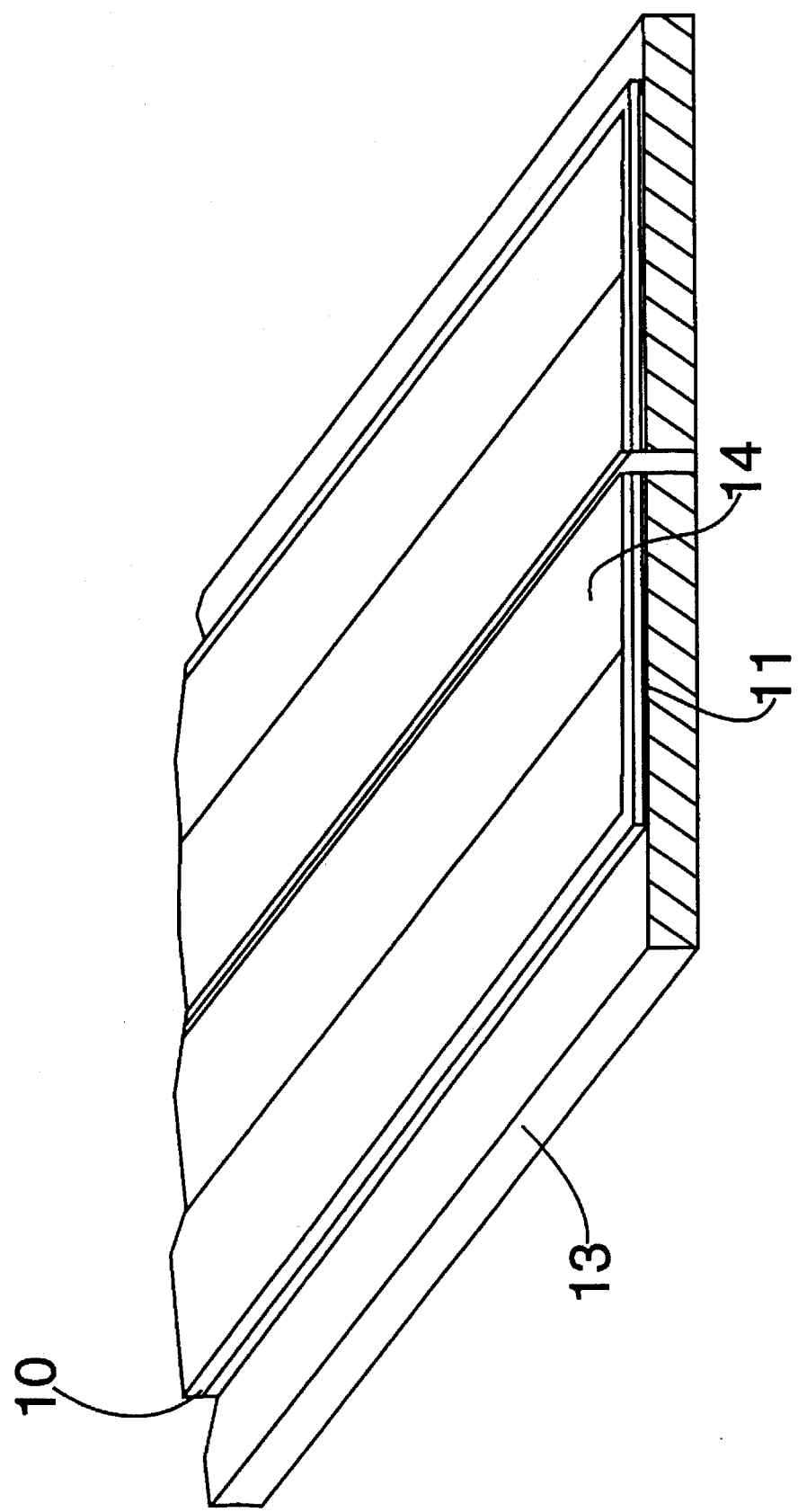

5,474,634

PROTECTIVE TAPE

BACKGROUND OF THE INVENTION

1. Field of the Invention

This invention is directed to strip tape devices for use especially in the trapping of particles generated when materials are sawed or cut. More specifically, it relates to a tape stripping to be used on orthopedic casting materials or like materials that tend to flake or dust and create unsightly and unhealthy volumes of saw dust.

2. Description of the Prior Art

In the field of orthopedic fracture reduction and in other areas where support materials are intended to be sawed, it is quite common in sawing the material to obtain large amounts of sawdust which fill the surrounding area in both an unsightly and unhealthy fashion. In an effort to solve the problem of dust accumulation, in the orthopedic area at least, it is quite common to either attach or have someone hold a vacuum device adjacent the areas that are being cut or sawed to suck away the sawdust formed in the process. When this is done in a hospital or doctor's office environment, the amount of noise from the vacuum is obtrusive and inconvenient. Moreover it involves extra equipment, auxiliary or extra personnel, and is, therefore, expensive.

Often no extra measures are taken to reduce the amount of cut particles and, thus, they are dispersed into the environment. When the cast material is plaster of paris or other synthetic materials such as fiberglass, the accumulation of the dust particles in the air can cause extremely troublesome dermalogical and pulmonary problems and also present a potentially hazardous condition for eye safety. It is therefore best to alter the technique in an effort to remove the dispersed particles or to avoid having them dispersed in the first place.

SUMMARY OF THE INVENTION

The purpose of the present invention is to provide a device in the form of tape stripping which in consequence of its configuration facilitates the isolation of sawed particles to the area of cutting as the material is being cut or sawed. Thus, for example, when a casting material is ready to be removed, the protective tape of the invention is applied to the cast in such a manner as to orient the cutting path preferably along the center of the tape. In a preferred case, a guide line is drawn on the tape for such purpose. The process of cutting generates the particles which instead of being dispersed into the atmosphere are accumulated on the adhesive surfaces of the trapping tape and also embedded into the body of the bottom layer of the tape thereby obviating the need for any vacuum equipment material and the associated personnel required therefor.

DESCRIPTION OF THE DRAWINGS

FIG. 1 is a perspective view of one embodiment of the tape stripping of the invention before being applied to the casting material or the material to be protected.

FIG. 2 is a perspective view of the tape of the invention just prior to being applied to a cast or the material to be protected.

FIG. 3 is a perspective view of the tape of the invention applied to the casting material with a saw cut therein demonstrating the results of using the tape on the cast.

The Figures are not drawn to scale.

DETAILED DESCRIPTION OF THE INVENTION

The operative layers of the tape device of the invention are uniquely configured and structured in such a way as to present a configuration which can be applied to casting material and remain in place during the cutting process. The composite structure utilizes as a base layer a support material which may be made of plastic or paper or some other material, natural or synthetic, the primary characteristic of which is that it is resilient enough to be applied over an irregular or curved surface and can be sawed or cut with standard saws or cutting materials used in the industry. The base layer has a thickness depending on the preferences of the ultimate user, but in general may be of the thickness of standard tapes such as cellophane tapes, packing or masking tape, duct tape, and the like provided the sticky surface applied to the cast holds the tape in place during cutting. In the drawings, the base layer is shown at number 10.

In the preferred embodiment, there are two layers of glue, although suitable results can be obtained with one layer when the criteria of the invention are followed. In the preferred embodiment, on each side of the base layer 10 are two layers of glue, layer 11 ( hereinafter sometimes called the pressure sensitive adhesive layer) when it is both the pressure sensitive adhesive layer and the layer which attaches the tape to the material and layer 12 of FIGS. 1 and 2. These layers serve several purposes. Layer 11 provides the means by which the base layer 10 is attached to the casting material and the means for providing a reservoir for cut particles. Layer 12 provides another "catching" layer. Because of variations in surface area of the various materials to be protected when sawed, it is often preferred to have a relatively thicker layer of glue as layer 11. The purpose here is not only to facilitate and improve the adherence of the pressure sensitive adhesive layer 11 to the cast material 13 ( FIG. 3 ) but also to provide a fuller "catching" reservoir. Thus in providing a tape device for the usual orthopedic casting materials, a tape having a glue thickness found in the ordinary cellophane or Scotch-brand type tape is not usually suitable because the degree of adherence is not great enough. In general, a thickness of glue for layer 11 is one which is both sufficient to maintain adherence during sawing including penetrating the irregularity of the cast material surface, but not so great as to either provide a gummy flowing layer or to foul the saw blade. It is desirable to have a thickness for layer 11 which is relatively and visibly thicker than layer 12 to provide a reservoir for particles that are cut from the cast material. Typically, thicknesses for layer 11 of the order of 0.5 mm to 2.5 mm are suitable and preferred.

The top or catch layer 12 is typically thinner than layer 11, but it does not have to be. The purpose here is to provide a glue which will hold the cut particles as the saw proceeds through the cast material even though it is expected that layer 11 will retain the majority of cast particles. In use, the particles will adhere to the edges of the glue layer 12 as well as glue layer 11. Typically, upper layers of the order of 25% to 100% of the thickness of layer 11 are suitable with 0.25 mm to 1.5 mm being preferred. Those skilled in the art will have available to them a variety of glue materials which may be used and in most cases this will depend on personal preference. The glue should not be one which hardens on exposure to air and should be stable at temperatures generated by the friction of the saw blade, say 150–180 degrees Fahrenheit. In experience, it has been found that soft, gummy-type cements such as rubber cements should be avoided because of the fouling effect that they have on the saw blade. On the other hand, soft, gel-like glues, especially for layer 11 are very desirable. The upper glue layer 12 can also contain a scoring or guide line 17 to permit the saw operator to follow a direct path on the casting material.

In a preferred embodiment, the device also includes a protective sheet 14 on the upper glue layer 12, the purpose of which is to obscure the bulk of the glue from the environment while the cast is being cut. This avoids the inconvenience of inadvertent touching of the glue surface by attending personnel. Prior to use, the protective sheet 14 is either folded back as shown in FIGS. 1 and 2 or can actually be shipped prior to use with the protective coating folded over the glue surface.

Another preferred aspect of the device of the present invention is the provision of protective coating layers 15 and 16 provided to cover the otherwise exposed glue surfaces during shipment and prior to use. Using the preferred aspects, the sheet of tape stripping is presented in a unitary form which may be packaged and shipped conveniently.

Alternatively, long sections of the stripping material can be rolled into convenient rolls and shipped and dispensed for use in that fashion.

Those skilled in the art will recognize that the tape without the folded protective sheet or the waxed protective paper can generically be called a double-sided tape. In general, commercially available double-sided tapes may be used in both the product and process of this invention provided that at least one adhesive layer of the tape is of sufficient adherence and thickness to provide a strong bond at the cast material surface so that it does not move when the sawing operation is in progress and to provide a suitably sized reservoir for the cut particles.

Other modifications of the product and process of the invention can be made as will be apparent to those skilled in the art. For example, while the bulk of the foregoing discussion is in the context of casting materials, it is obvious that the invention will work as well on any other materials required to be sawed. Other variations can be made and still remain within the inventive concept.

What is claimed is:

1. A method of containing particles generated by the cutting of an orthopedic casting material subjected to a cutting process which comprises applying a tape strip to the surface of the orthopedic casting material to be subjected to the cutting process, said tape strip comprising two surfaces, one of which carries a pressure sensitive adhesive layer adapted to be applied to the surface to be cut, said pressure sensitive adhesive layer being sufficiently adherent to retain the tape strip in position when the orthopedic casting material is cut, and wherein said pressure sensitive adhesive layer is of sufficient thickness and tackiness to facilitate capture of material particles when the casting material is cut and to minimize fouling of a cutting blade, wherein the cutting is through the tape strip, whereby the particles generated in the cutting process adhere to the tape strip.

2. The method of claim 1 further comprising a second glue layer as the second surface.

3. The method of claim 2 wherein the pressure sensitive adhesive layer is relatively thick compared to the glue layer on the second surface.

4. The method of claim 3 wherein the pressure sensitive adhesive layer is from 0.5 mm to 2.5 mm.

5. The method of claim 4 wherein the pressure sensitive adhesive and the top surface are protected by protective layers which aid in preventing the strip from sticking to objects other than the one to be cut.

6. The method of claim 4 wherein the glue surface and the pressure sensitive adhesive layer are relatively gummy, spongy layers which are relatively stable at elevated temperatures.

\* \* \* \* \*